United States Patent [19]

Barth

[11] Patent Number: 5,183,064
[45] Date of Patent: Feb. 2, 1993

[54] DENTAL CLEANSING DEVICE AND INTERDENTAL FLOSS FOR SUCH A DEVICE

[76] Inventor: Frederic Barth, 11, Place du Marché, Chevry II, F-91190 Gif-sur-Yvette, France

[21] Appl. No.: 815,035

[22] Filed: Dec. 31, 1991

Related U.S. Application Data

[62] Division of Ser. No. 452,354, Dec. 19, 1989, Pat. No. 5,094,256.

[30] Foreign Application Priority Data

Dec. 19, 1988 [FR] France ........................ 88 16729
Apr. 27, 1989 [FR] France ........................ 89 05618
Jun. 27, 1989 [FR] France ........................ 89 08509

[51] Int. Cl.$^5$ ............................................. A61C 15/00
[52] U.S. Cl. ............................ 132/323; 132/321; 132/322; 132/329
[58] Field of Search ............... 132/321, 322, 323, 324, 132/325, 326, 327, 329

[56] References Cited

U.S. PATENT DOCUMENTS

| | | | |
|---|---|---|---|
| 2,516,539 | 7/1950 | Atols | 132/326 |
| 2,612,177 | 9/1952 | Footer | 132/324 |
| 3,106,216 | 10/1963 | Kirby | 132/326 |
| 3,472,247 | 10/1969 | Borsum et al. | 132/322 |
| 3,747,612 | 7/1973 | Davis | 132/324 |
| 3,814,114 | 6/1974 | Roberts | 132/326 |
| 3,930,059 | 12/1975 | Wells | 427/2 |
| 4,013,085 | 3/1977 | Wright | 132/323 |
| 4,031,908 | 6/1977 | Ting | 132/322 |
| 4,319,592 | 3/1982 | Ulrich | 132/322 |
| 4,655,233 | 4/1987 | Laughlin | 132/323 |
| 4,883,080 | 11/1989 | Lang | 132/322 |

FOREIGN PATENT DOCUMENTS

| | | |
|---|---|---|
| 0001044 | 3/1979 | European Pat. Off. . |
| 0037434 | 11/1980 | European Pat. Off. . |
| 3642361 | 4/1988 | Fed. Rep. of Germany . |
| 1119083 | 6/1956 | France . |
| 584030 | 1/1977 | Switzerland . |

*Primary Examiner*—Cary E. O'Connor
*Attorney, Agent, or Firm*—Oliff & Berridge

[57] ABSTRACT

A dental device for cleaning teeth includes a fork-shaped instrument with two arms, each arm having a free end and a needle eye near the free end, where the two arms are separated by a predetermined distance at a point of the needle eyes. A dental floss for use with the dental device includes a guide rod connected to one end of the dental floss and a stop button connected to another end of the dental floss such that the floss can be securely mounted to the forked-shaped instrument. The guide rod and stop button can be integrally molded with the dental floss, the entire assembly made from a strong, plastic material.

17 Claims, 6 Drawing Sheets

DENTAL CLEANSING DEVICE AND INTERDENTAL FLOSS FOR SUCH A DEVICE

This is a division of application Ser. No. 452,354 filed Dec. 19, 1989, now U.S. Pat. No. 5,094,256.

FIELD OF THE INVENTION

The present invention relates to a dental cleansing device capable of being connected to a pressurized fluid supply device, in order to produce a dental cleansing effect by a jet of water. The invention also relates to an interdental floss which is to be used on a dental cleansing device comprising a fork-shaped instrument with two arms, each of which has a needle eye in the vicinity of its free end, the two needle eyes being aligned in order to receive a piece of interdental floss. The invention furthermore relates to a dental cleansing device with improved means for securing such a piece of interdental floss.

BACKGROUND OF THE INVENTION

In every human being w teeth, mastication inevitably causes food to infiltrate between the teeth. Failure to remove the resulting food deposits is the source of proximal caries and periodontal diseases.

Using a toothbrush does not allow these anatomical spaces to be cleansed, which spaces are, on the other hand, accessible to the interdental jets of water from devices known as pressurized fluid supply devices to interdental floss and other stiff interdental brushes and interdental tooth picks. Ideal interdental hygiene consists in simultaneously employing interdental floss and jets.

By means of a mechanical effect, interdental floss enables fibres of food wedged at the very contact point to be dislodged, something which a jet cannot do, and then, by small up and down movements, the mesial and distal faces of the two adjacent teeth to be scraped. It is the use of interdental floss which enables approximal caries to be prevented at the contact point. Floss is superior to the action of the jet in this context since it definitively dislodges the fibres wedged at the very contact point, whereas the jet cannot manage this. By its mechanical scraping action, floss is furthermore superior to the jet in the quality of the surface finish obtained.

On the other hand, the jet has the advantage of being able to dislodge rapidly the food deposits which have already passed below the contact point and which may be removed laterally by water pressure. However, in addition to the less satisfactory quality of the surface finish obtained, the jet may be dangerous to use. Indeed, especially when the pressure is set to its strongest, it is imperative that the jet be prevented from being directed obliquely in the tooth-gingiva direction, which would in the long term cause the gingiva to become detached. The danger then arises that daily use of the jet becomes a contributory factor in periodontal decay.

In order not to cause any harm, the jet would then have to be handled precisely and judiciously, in other words continually controlling the direction of the water jet perpendicular to the major axes of the teeth or obliquely in the gingiva-tooth direction.

It proves to be very difficult, or even impossible, in practice with the known pressurized fluid supply devices to control perfectly this optimum directing into all the interdental spaces of the same mouth, the jet being produced through a tooth pick which is simply held in the hand.

Through ageing or periodontal disease, the gingival papilla may retract and disappear. The resulting wide open embrasures are readily filled with food deposits which may be easily cleansed with a well directed jet or an interdental radial (hair) brush mounted on a handle or some other toothpick.

Among the various interdental floss systems, there are disposable floss-holders with a piece of interdental floss crimped onto the free ends of the two arms of a fork. Other interdental floss system have a fork-shaped floss-holder with two needle eyes through which the floss is to be threaded, which is a difficult operation. There are, moreover, interdental floss systems with a fork having notches for receiving the floss in its two arms, which arrangement simplifies the positioning of the floss but the securing of the floss in these notches is uncertain during assembly and use, in particular when it is being disengaged from the contact point.

Lastly, it is already known from U.S. Pat. No. 4,031,908 to provide, on the same dental cleansing device, the use of a piece of interdental floss held between the two arms of a fork, and the use of a jet of water emitted by one of the arms of the fork towards the other arm, adjacently to the position of the interdental floss. This known device has, however, a certain number of disadvantages.

As a result of the presence of a single jet of water, this device only allows rinsing in one direction with a single operation, rinsing in both directions requiring a double operation. Now it often happens that rinsing in only one direction does not enable the food deposits in the two interdental embrasures, the vestibular and lingual, to be dislodged correctly.

Moreover, in order to make this double operation possible, the fork of this known device must be a flat fork, whereas an interdental floss-holder must preferably have the shape of a curved fork in order to make correct access to all the teeth possible.

As a result of this need for a double operation, the jet of water may, in addition, be designed uniquely so as to act perpendicular to the major axes of the teeth since, if the jet is inclined, it would be directed correctly in the gingiva-tooth direction during the first operation, but would necessarily be directed in the wrong direction, that is the tooth-gingiva direction during the second operation, after turning the device around by 180°.

In addition to these problems caused by the presence of a single jet of water, it must be noted that with this known device, replacing a length of broken interdental floss by a new length of interdental floss, and the correct tensioning of this length of interdental floss, present difficulties to the extent that, on one hand, the two needle eyes provided at the free end of the two arms of the fork are very fine so that it is not easy to thread the interdental floss through these needle eyes and that, on the other hand, locking of the interdental floss with tension is effected by clamping the two ends of the floss between the body (handle) of the device and the fork-shaped head, the said two parts being connected by screwing.

SUMMARY OF THE INVENTION

The subject of the present invention is a dental cleansing device providing complete cleansing of the interdental spaces in a single operation. The subject of the invention is also a dental cleansing device providing improved cleansing by means of a jet of water, the jet of water being always correctly oriented in the gingivatooth direction. The subject of the invention is furthermore a dental cleansing device designed so as to enable simultaneous cleansing by a jet of water and by interdental floss and/or by a radial (hair) or axial (hair) brush or brushes. The subject of the invention is, in addition, interdental floss which can be mounted and held taut in a simple and reliable manner on a fork-shaped floss-holder with two arms. The subject of the invention is also a set of several pieces of interdental floss which is simple to manufacture and convenient to use. The subject of the invention is lastly a dental cleansing device having means for locking a tensed piece of interdental floss simply, quickly and reliably.

The dental cleansing device according to the invention comprises a fork-shaped instrument with two arms capable of being connected to a pressurized fluid supply device. According to the invention, each of the two arms has, on its internal face, an orifice for ejecting a water jet, the two orifices being directed so as to enable the ejection of two non-aligned water jets in opposite directions.

The two water jets, with opposite directions but non-aligned, ensure in a single operation cleansing of the two vestibular and lingual interdental embrasures, the cleansing efficiency being greatly improved by the rotational effect (vortex) which the two jets, directed so as not to meet each other, produce. In addition, the successive action of the two opposing jets in the same embrasure produces a push-pull effect on the food deposits located thereon which proves to be particularly effective for dislodging and removing them.

The two orifices for ejecting water jets may advantageously be directed so as to enable the ejection of two parallel offset water jets, which, when the instrument is positioned obliquely relative to the teeth, increases the probability that at least one of the jets reaches each interdental embrasure with a high degree of efficiency.

The two orifices are preferably directed so as to enable the ejection of two oblique water jets converging in the gingiva-tooth direction, which ensures that the two jets are directed correctly at all times.

It is also possible, within the scope of the invention, to provide in each arm of the fork-shaped instrument several orifices enabling the ejection of multiple water jets or sprays.

The device according to the invention may, in addition, comprise, on the fork-shaped instrument with two arms producing two opposing water jets, two needle eyes for the threading and securing of a piece of interdental floss in the vicinity of the free end of the said two arms. In this case, the said needle eyes arranged in immediate proximity to the said orifices are dimensioned and directed so as to enable, as desired, the threading and securing of a piece of interdental floss and/or the securing of radial (hair) or axial (hair) brushes. The device according to the invention may thus be employed simultaneously as a double water jet and interdental floss, the two cleansing actions complementing each other. If, with ageing, the interdental spaces become denuded, the floss may advantageously be replaced by radial (hair) or axial (hair) brushes wedged into the guide needle eyes. The simultaneous securing of a piece of interdental floss and radial (hair) or axial (hair) brushes is also possible The interdental floss according to the invention which is to be used on a dental cleansing device comprising a fork-shaped instrument with two arms, each of which has a needle eye in the vicinity of its free end, the two needle eyes being aligned, consists of a length of floss which is sufficiently long to enable it to be fitted onto the said instrument. One end of this length of floss is integral with a guide rod whose length is greater than the space between the two arms of the instrument at the point of the said needle eyes, and the other end is integral with a stop button.

As a result of the guide rod, the length of floss may be threaded simply and quickly through the needle eyes of the instrument. After the threading, the user pulls on the guide rod until the stop button provided at the other end of the piece of floss comes to rest from the outside against one of the arms of the fork, which operation locks the said end of the piece of floss relative to the instrument. Then one need only pull the piece of interdental floss taut by exerting a tensile force on the end integral with the guide rod, and lock this end of the piece of floss onto the instrument, for example around winding catches of a type known per se provided on the instrument.

The mushroom-shaped stop button of the piece of interdental floss may advantageously have a head and a foot enabling the button to be held by friction or by snap-catching in the needle eye in the event of the length of floss breaking in the mouth.

In order to improve the grip, the guide rod integral with one end of the length of floss may have a gripping protuberance at its free end.

To further simplify the fitting of the piece of interdental floss on the instrument, and in particular to simplify the tensioning and fastening of the tensed piece of interdental floss on the instrument, it is provided, according to another feature of the invention, that the piece of interdental floss bearing a stop button at one end and a guide rod at its other end is of a calibrated length. In this case, the fork-shaped instrument which is to receive this piece of interdental floss bears one-step means for receiving and with locking the guide rod the piece of interdental floss in the taut state.

These means provided on the fork-shaped instrument may consist of a split guide stop for receiving and serving as a stop for the end of the guide rod turned towards the stop button, and a clamp for securing and locking the said rod against the instrument.

According to another embodiment, the guide rod of the piece of interdental floss may have a series of transverse serrations or notches distributed over its length, the fork-shaped instrument having, in order to receive the guide rod, a clamp comprising teeth capable of interacting with the serrations of the guide rod in order to lock the latter with the piece of interdental floss in the taut state.

In the two embodiments, the pieces of interdental floss having a stop button at one end and a guide rod at the other end may advantageously be manufactured and marketed in the form of a set of several lengths of floss arranged side by side in a plane, the stop buttons and guide rods of which are connected by fragile parts of small cross-section to two opposite limbs of a frame moulded from plastic in a single piece with the stop buttons and the guide rods, the ends of the pieces of floss being integrally moulded with the stop buttons and with the guide rods.

BRIEF DESCRIPTION OF THE DRAWINGS

With reference to the attached drawing, several guiding and non-limiting embodiments of the dental cleansing device according to the invention will be described hereinbelow in more detail; in the drawings.

DETAILED DESCRIPTION OF THE PREFERRED EMBODIMENTS

Figure 1:
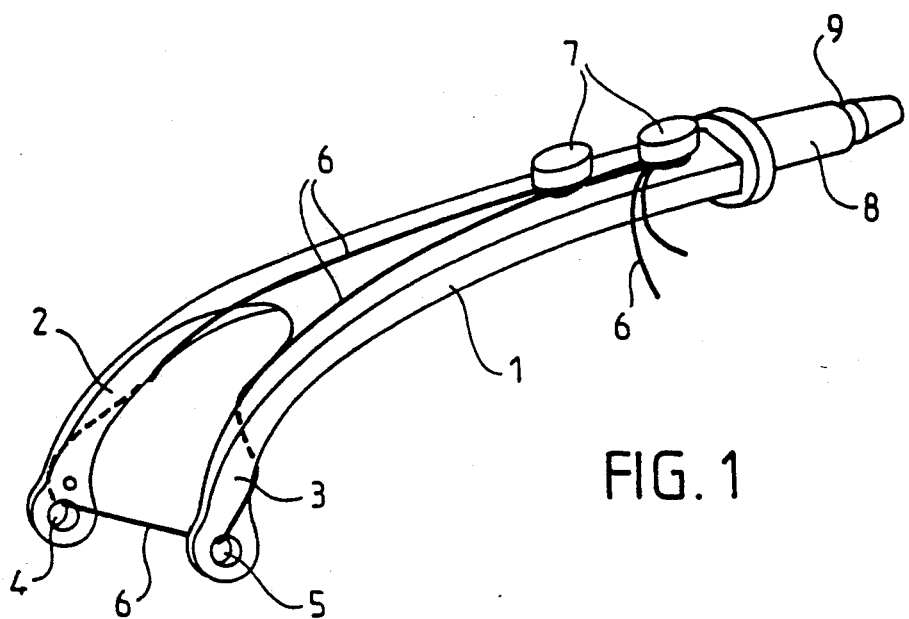
FIG. 1 is a perspective view of a fork-shaped instrument serving as an interdental floss-holder.

In FIG. 1, a dental cleansing instrument comprises a body 1 terminating at one end in a fork with two arms 2, 3. The two arms 2, 3 of the fork are inclined relative to the body 1 so that the common plane of the arms 2, 3 forms, at the free end of the arms, an angle of approximately 45° with the plane of the body 1 of the instrument, the two arms 2, 3 opening out from each other symmetrically relative to the longitudinal axis of the body 1.

In the vicinity of their free end, the arms 2 and 3 of the body 1 have two aligned needle eyes 4 and 5 through which passes a piece of interdental floss 6, the two ends of which are wound up and wedged onto two catches 7 arranged on the body 1.

At its opposite end, the body 1 terminates in a joining piece 8 for fitting into the handle of a pressurized fluid supply device as described in more detail with reference to FIG. 2. The joining piece 8 has a throat 9 corresponding to a sealing strip contained in the handle of the pressurized fluid supply device and a coloured shoulder is provided between the body 1 and the joining piece 8 in order to distinguish the instrument.

Figure 2:
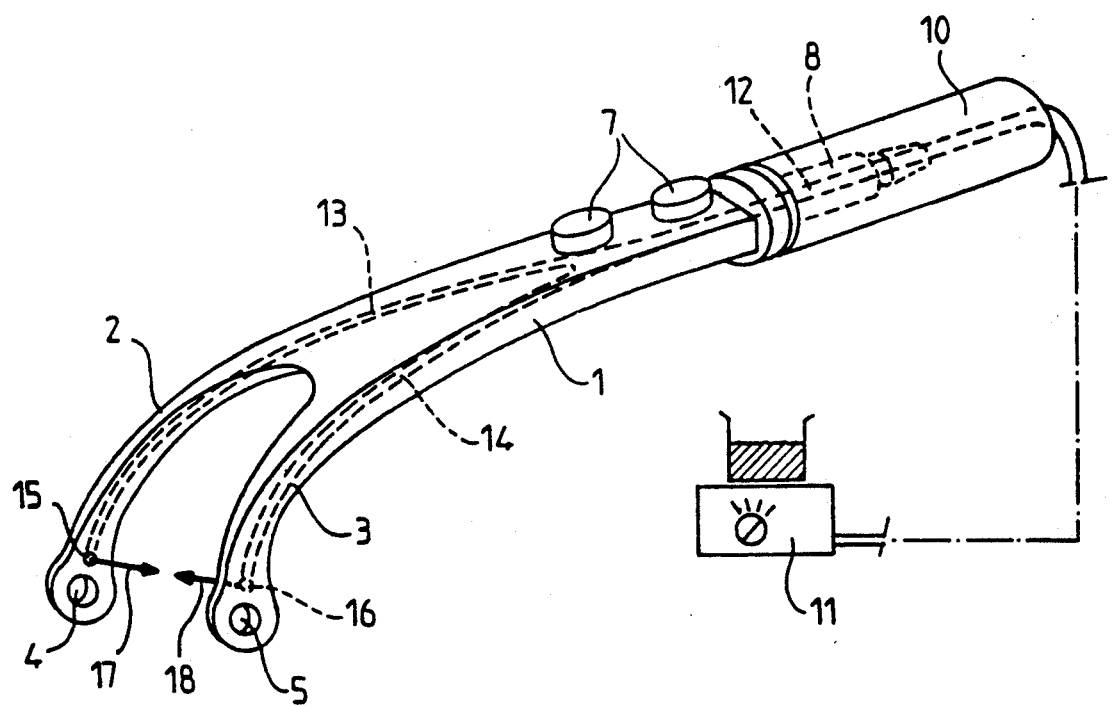
FIG. 2 is a perspective view of this same instrument connected to a water pik in order to serve as a twin water-jet dental cleansing device.

In FIG. 2, in which the body 1 of the instrument is joined to the handle 10 of a pressurized fluid supply device 11, it can be seen that the joining piece 8 and the body 1 are traversed by a duct 12 which, inside the body 1, divides into two ducts 13 and 14 ending in the vicinity of the free ends of the arms 2 and 3 where they open out, in proximity to the needle eyes 4 and 5, onto the inner face of the arms, through two orifices 15 and 16 directed such that they enable the ejection of two water jets 17 and 18 in opposite directions when the pressurized fluid supply device 11 is operating.

Figure 3:
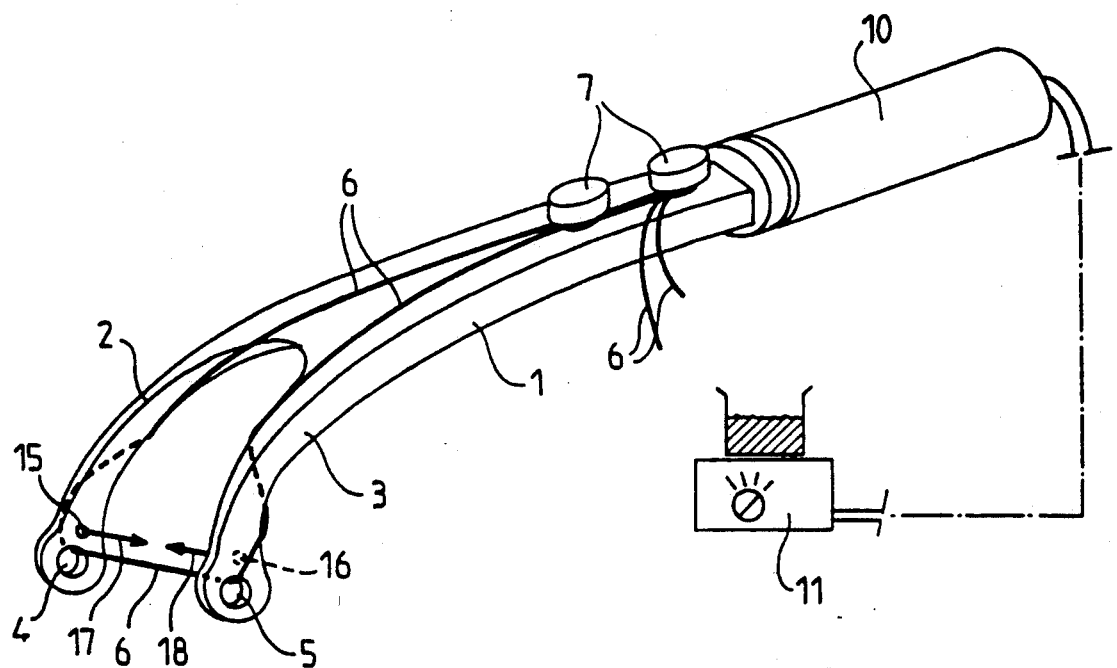
FIG. 3 is a perspective view of this same instrument in its twin functions as an interdental floss-holder and twin water-jet dental cleansing device.

In FIG. 3, the instrument according to FIGS. 1 and 2 is employed simultaneously as a cleansing instrument with a piece of interdental floss 6 as in FIG. 1 and as a cleansing instrument with two water jets 17, 18 as in FIG. 2.

Figure 4:
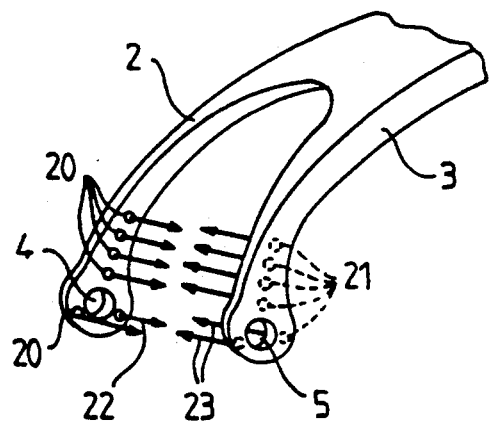
FIG. 4 shows a variant of the instrument with multiple water jets being produced by each arm of the fork-shaped instrument.

In the variant shown in FIG. 4, the two orifices 15 and 16 provided according to FIG. 2 in the two arms 2 and 3 of the fork in order to produce two water jets 17, 18 from opposite directions are replaced by a plurality of orifices 20 and 21 producing two multiple jets 22 and 23 forming two sprays from opposite directions.

With regard to the two water jets 17, 18 from opposite directions in FIGS. 2 and 3, and similarly the two multiple water jets 22, 23 from opposite directions in FIG. 4, it should be noted that these jets are parallel but are offset in the direction of the length of the body 1 of the instrument, as is clearly visible in FIGS. 2 to 4.

Figure 5:
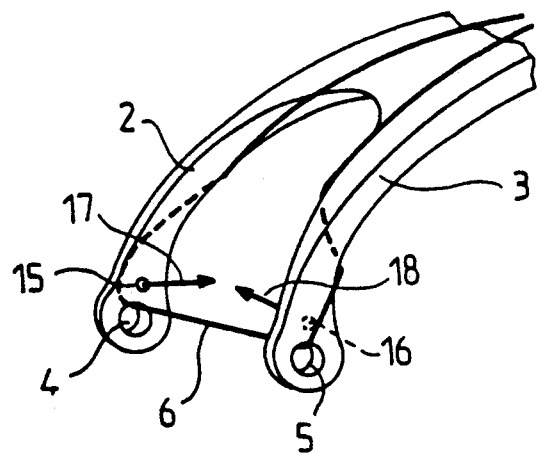
FIG. 5 shows a variant of the instrument with two oblique water jets converging in the gingiva-tooth direction.

In FIG. 5, the two orifices 15 and 16 provided in the two arms 2 and 3 are directed so as to produce two oblique water jets 17 and 18 inclined in the gingivatooth direction. The two jets are thus directed properly with no risk of causing detachment of the gingiva prejudicial to good periodontal health.

Figure 6:
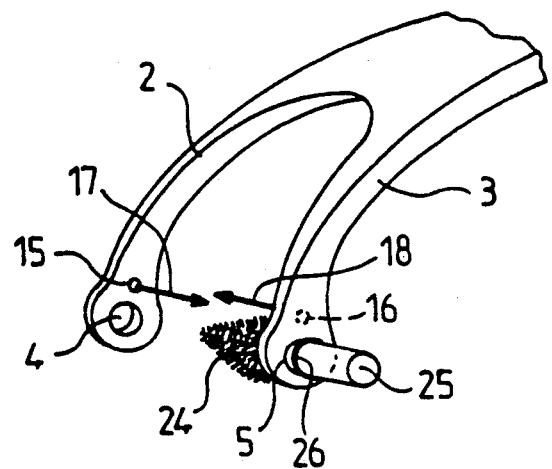
FIG. 6 shows the instrument in its twin water jet and radial (hair) brush-holder version.

In FIG. 6, one of the two needle eyes 4 and 5, namely the needle eye 5 of the arm 3 of the fork-shaped instrument, receives a radial (hair) brush 24, the body 25 of which is fitted from inside the fork into the needle eye 5 and is held therein by friction or by a catching shoulder or ring 26, such that the radial (hair) brush 24 projects from the arm 3 towards the other arm 2.

The needle eye 4 of the other arm 2 may, of course, also receive a radial (hair) brush of this type directed towards the arm 3.

Figure 7:
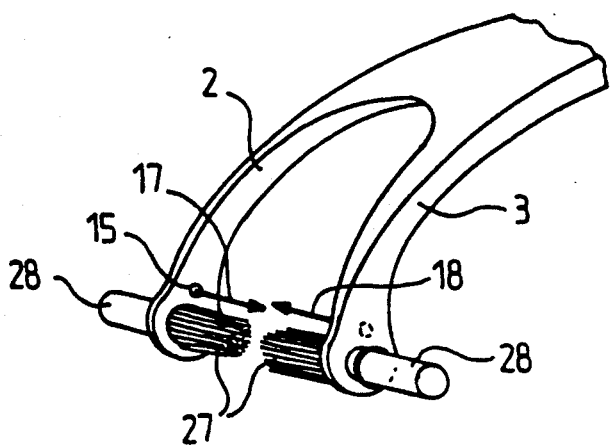
FIG. 7 shows the instrument in its twin water jet and axial (hair) brush-holder version.

In FIG. 7, two axial (hair) brushes 27 are fastened into the two needle eyes of the two arms 2 and 3, their bodies 28 being fitted and held by friction or catching in the same way as for the radial (hair) brushes in FIG. 6.

It should be noted that both the radial (hair) brushes 24 in FIG. 6 and the axial (hair) brushes 27 in FIG. 7, which can be used preferably simultaneously with a twin water jet 17, 18, may also be used simultaneously with a piece of interdental floss 6 according to FIGS. 1, 3 and 5, the needle eyes 4 and 5 enabling both the passage of a piece of interdental floss 6 and the fitting of the bodies 25, 28 of the radial (hair) brushes 24 or axial (hair) brushes 27.

The piece of interdental floss 6 used in the embodiments described so far consists of a length of interdental floss drawn from a commercial coil of floss. During use, a piece of floss of this type breaks at least once during the complete cleansing of all the interdental spaces. It must therefore be changed at least once during each use.

This changing operation consists of unwinding and cutting off a sufficient length of floss from a coil and attaching one end onto the body of the instrument, for example onto the catches 7. The other end of the piece of floss is then passed through the needle eyes 4 and 5. Fitting of the piece of floss is completed by pulling the latter taut by applying a tensile force to the other end before attaching this other end onto the body of the device, for example onto the catches 7.

In practice, this operation of changing the floss is performed more or less easily according to the dexterity of the user. In order to change the piece of floss, it is in fact necessary a) to unwind a sufficient length of floss from the coil (not too long in order to avoid waste, not too short as then it is impossible to fit the piece of floss), b) to fit the piece of floss by leading it along a particular path and by passing it through the needle eyes, which operation, even with needle eyes of a diameter which is markedly greater than the diameter of the piece of floss, requires a degree of dexterity and takes up some time; c) to effect this fitting generally with wet hands, which causes the piece of floss to cling and become unable to be guided easily.

Figure 8:
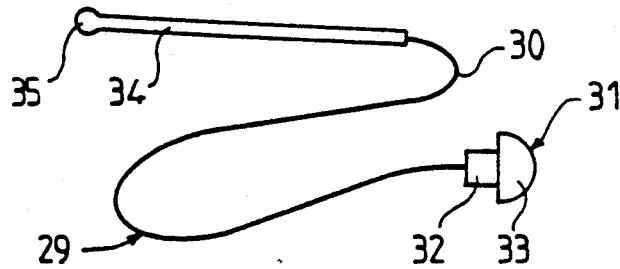
FIG. 8 shows an embodiment of the interdental floss according to the invention.

FIG. 8 shows a piece of interdental floss which considerably simplifies the fitting of the piece of floss onto the body of the instrument and enables the piece of floss to be changed quickly.

In FIG. 8, the piece of interdental floss 29 consists of a length of interdental floss 30 which is sufficiently long to enable it to be installed on an instrument according to FIGS. 1 and 3. The length of floss 30 has, at one of its ends, a mushroom-shaped stop button 31 comprising a foot 32, the diameter of which is essentially equal to the diameter of the needle eyes 4 and 5, and a head 33.

At its other end, the length of floss 30 has a rectilinear guide rod 34 exhibiting, at its free end, a gripping protuberance 35, the diameter of which is less than the diameter of the needle eyes 4 and 5. The length of the guide rod 34 is greater than the distance separating the two arms 2 and 3 of the body of the instrument 1 at the point of the needle eyes 4 and 5.

Figure 9A:
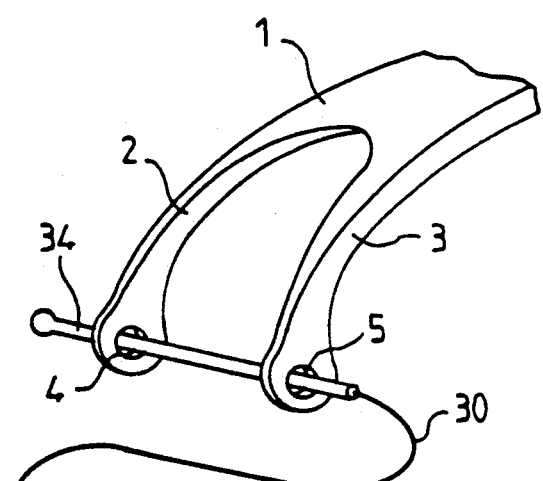
FIGS. 9a to 9d illustrate the fitting of a piece of interdental floss according to FIG. 8 onto a fork-shaped instrument according to FIGS. 1 to 3.
Figure 9B:
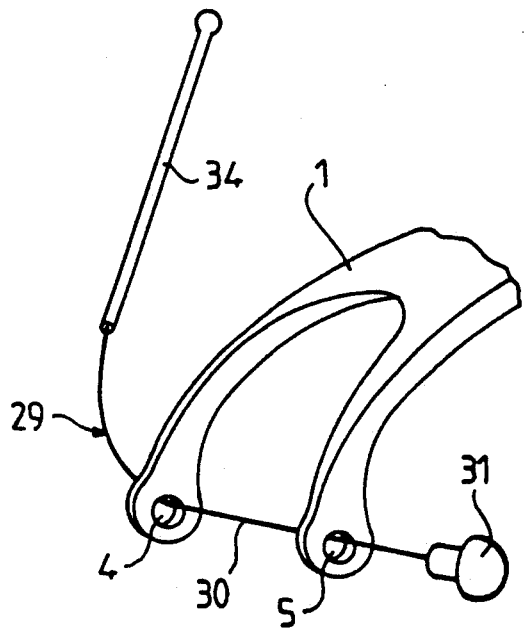
Figure 9C:
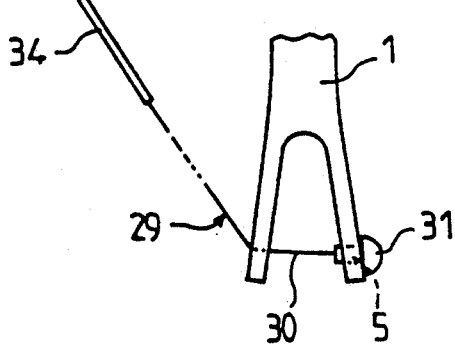
Figure 9D:
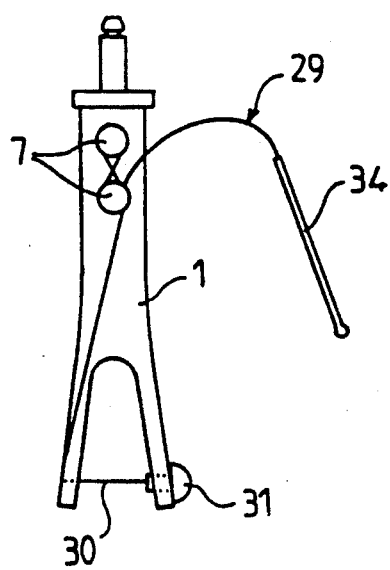
Figure 10:
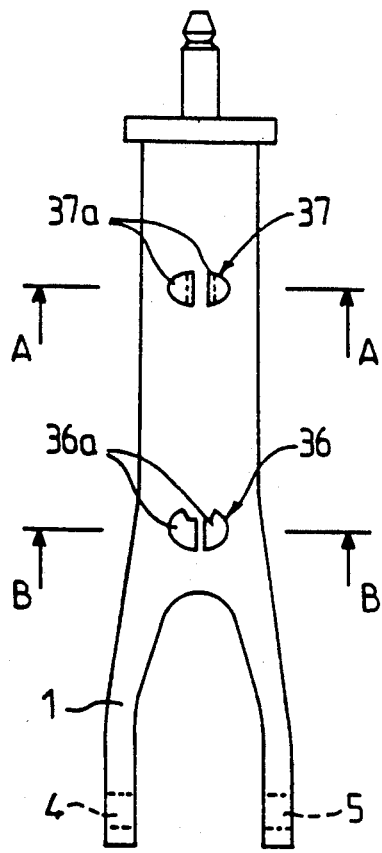
FIG. 10 shows a fork-shaped instrument with means for locking the piece of interdental floss quickly.

In FIGS. 9a to 9d fitting of the piece of interdental floss 29 according to FIG. 8 consists in passing the guide rod 34 of the piece of floss 29 directly through the two needle eyes 4 and 5 (FIG. 9a) which must exhibit a diameter greater than the maximum diameter of the guide rod 34 (at the point of the protuberance 35), in then pulling the piece of floss 29 through the two needle eyes 4 and 5 (FIG. 9b) until the foot 32 of the button 31 is inserted in one of the needle eyes, in this case the needle eye 5 (FIG. 9c), in pulling taut the piece of floss 29 and in finally attaching it to the body 1 by winding it around and by locking it on the catches 7 (FIG. 9d).

It would, of course, also be possible to lock the piece of floss 29 onto the body of the instrument 1 by means other than the catches 7, for example clip or snap-catch or similar systems.

In order to prevent traumas of the buccal mucosa, the head 33 of the stop button 31 exhibits a rounded shape, preferably a hemispherical shape.

The foot 32 of the stop button 31 is advantageously shaped so as to enable it to be held by friction or by catching in one of the needle eyes 4, 5 when the length of floss 30 breaks in the mouth.

The piece of interdental floss 29 according to FIG. 8 may be provided with its stop button 31 and its guide rod 34 by integral injection moulding of rigid plastic material.

Figure 11:
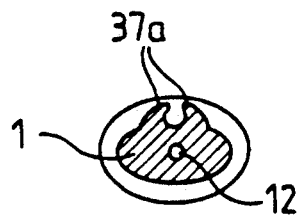
FIGS. 11 and 12 are sections along A—A and B—B in FIG. 10.
Figure 12:
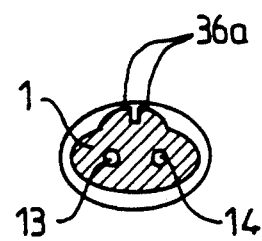
Figure 13:
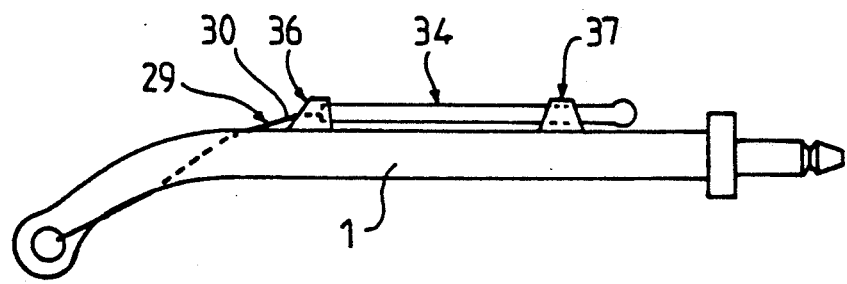
FIG. 13 is a side view of the fork-shaped instrument in FIG. 10 with a piece of interdental floss locked onto the instrument.

FIGS. 10 to 13 illustrate a preferred embodiment of the means provided on the instrument body 1 with a view to locking the piece of interdental floss 29 according to FIG. 8 quickly. The body 1 has in this case, on its upper side, a split guide stop 36 in the front part of the instrument body 1, and a securing clamp 37 in the rear part of the body 1. The guide stop 36 comprises two rigid projections 36a formed from a single piece with the body 1 and separated from each other by narrow longitudinal slot (see FIG. 12) enabling the passage of the length of floss 30. The position of the guide stop 36 on the body 1 is selected in dependence on the length of the length of floss 30 between the stop button 31 and the guide rod 34 such that the length of floss 30 fitted according to FIGS. 9a to 9c may be locked in its taut state simply by fastening the guide rod 34 behind the guide stop 36 in the manner visible in FIG. 13. The securing clamp 37 has, as FIG. 11 shows, two elastic spaced projections 37a between which the guide rod 34, fastened behind the guide stop 36, may be introduced by elastic snap-catching and be held against the instrument body 1.

Correct operation of this system for locking the piece of interdental floss 29 entails, of course, the use of a piece of interdental floss 29 with a calibrated length and an accurate positioning of the guide stop 36 on the body 1 of the instrument so that the piece of interdental floss 29 is pulled perfectly taut when it is locked by the guide stop 36.

Figure 14:
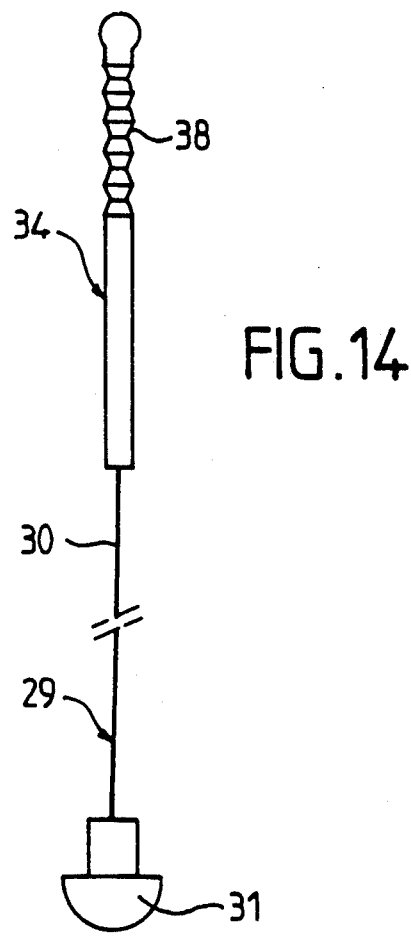
FIG. 14 shows a piece of interdental floss with a guide rod having serrations or notches for adjusting the tension.
Figure 15:
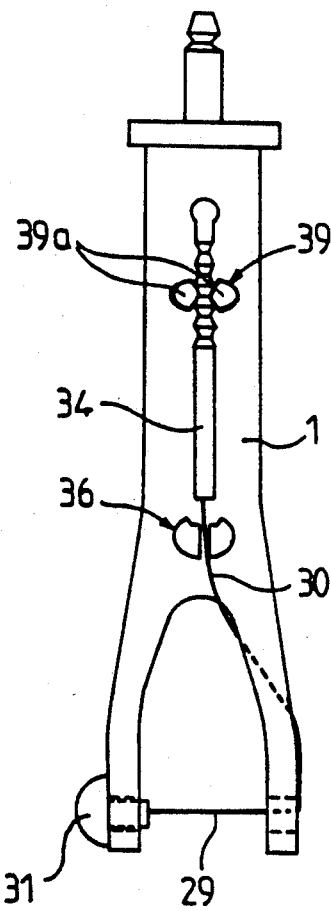
FIG. 15 shows a fork-shaped instrument with means for adjustably guiding and locking a piece of interdental floss according to FIG. 14.

FIGS. 14 and 15 illustrate a variant in which the guide rod 34 of the piece of interdental floss 29 has a longitudinal series of transverse serrations or notches 38. The body 1 of the instrument has in this case, in place of the securing clamp 37 according to FIGS. 10 to 13, a hooking clamp 39 having two opposing tapered teeth 39a between which the guide rod 34 of the piece of interdental floss 29 may be inserted at the point of its serrations or notches 38. After fitting the piece of interdental floss 29 onto the instrument body 1 in the manner illustrated in FIGS. 9a to 9c, the piece of floss 29 is thus held taut and locked in the taut state on the body 1 by the insertion of its guide rod 34 into the clamp 39 at the point of one of its notches 38, which immobilises the rod 34 relative to the body 1.

This embodiment of the piece of interdental floss 29 and of the instrument body 1 consequently enables the tension of the piece of interdental floss 29 to be adjusted and the manufacturing tolerances, in particular of the piece of floss 29, to be compensated for.

Although the guide stop 36 is provided on the instrument body 1, it no longer serves as a stop here, but simply as a guide for the length of floss 30 of the piece of interdental floss 29. This guide could be replaced by any other guide means acting on the piece of floss 30 or on the rod 34, or could also optionally be removed.

Figure 16:
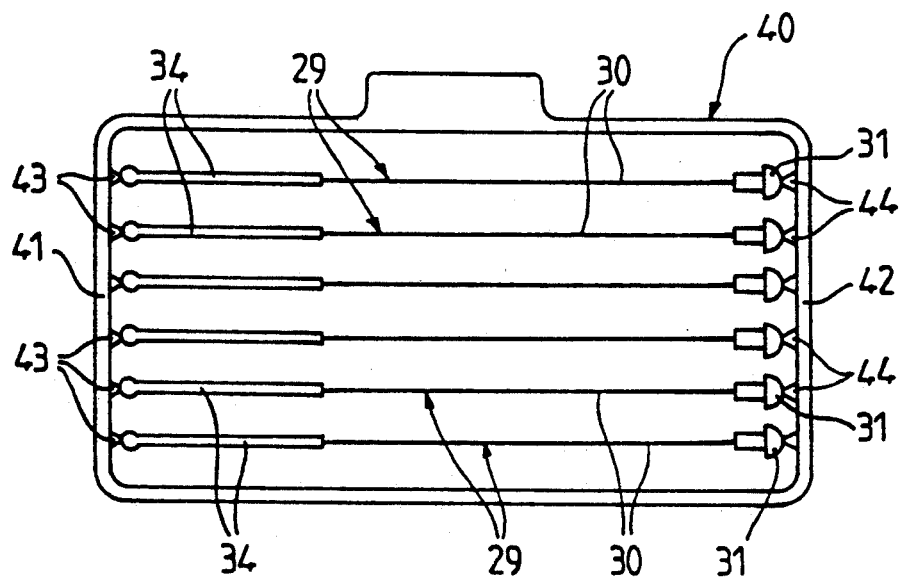
FIG. 16 shows a set of pieces of interdental floss according to the invention.

FIG. 16 shows a set of several pieces of interdental floss 29 with a particularly advantageous design from the point of view of manufacturing and marketing. Several lengths of interdental floss 30, each having a stop button 31 and a guide rod 34, are arranged here side by side in a plane, inside a rectangular frame 40. The guide rods 34 and the stop buttons 31 are moulded from plastic in a single piece with two opposite limbs 41 and 42 of the frame 40, with the ends of the sections of floss 30 being integrally moulded, the guide rods 34 and the stop buttons 31 being connected to the limbs 41 and 42 of the frame 40 by fragile parts 43, 44 of small cross-section.

In order to detach a piece of interdental floss 29 from this set with a view to fitting it onto the dental cleansing instrument, one need only exert a sufficient force on the stop button 31 and on the guide rod 34 of this piece of floss 29, relative to the limbs 42 and 41 of the frame 40, to break the fragile parts 44, 43 and to thus free the piece of interdental floss 29.

This embodiment may, of course, be applied equally well to the pieces of interdental floss in FIG. 8 and those in FIG. 14.

It should be noted that though, in the embodiments illustrated, the instrument body 1 is always shown as being intended to be coupled to the handle of a water pik, the piece of interdental floss 29 according to FIGS. 8 and 14 could, within the scope of the invention, be used on instrument bodies 1 provided to serve only as an interdental floss-holder, and not as a dental cleansing instrument with a twin water jet as well.

Although the cleansing instrument with a twin water jet according to all the embodiments shown consists of a fork-shaped body which can serve at the same time as an interdental floss-holder, it is similarly possible, within the scope of the invention, to use this cleansing system with a twin water jet on a fork-shaped instrument provided solely for this function, in other words without the two needle eyes 4 and 5 which can receive a piece of interdental floss and/or radial (hair) brushes and/or axial (hair) brushes.

I claim:

1. An interdental cleansing device, comprising:
a fork-shaped instrument having a body and two separated arm extending from an end of said body, each said arm having a free end and a needle eye of predetermined cross section near its free end, the two arm being separated by a predetermined distance at a point of said needle eyes;
a dental floss adapted for being fitted onto said instrument so as to pass through and extended between the needle eyes of the two arms, wherein said dental floss comprises a floss portion having two opposite ends, a length of said floss portion between said two opposite ends greater than said predetermined distance, the floss portion being provided at one of its ends with a guide rod having a cross section smaller than the needle eyes and being provided at another of its ends with a stop button having a cross-section greater than the needle eyes, and said fork-shaped instrument further comprises a guide stop attached to said body and adapted for stopping the guide rod, whereby the location of the guide stop on the instrument body with respect to the needle eyes and the length of the floss portion are related to one another such that with the floss portion being fitted onto the instrument, with the stop button stopped at one needle eye and the guide rod locked behind the guide stop, the floss portion is pulled taut.

2. The device of claim 1, wherein the guide rod has a length greater than said predetermined distance.

3. The device of claim 1, wherein the guide stop has an opening therein providing passage for the floss portion, the guide stop retaining an end of the guide rod nearest the floss portion.

4. The device of claim 1, wherein the stop button is a mushroom-shaped button with a head and with a foot, the foot having a cross section adapted to be frictionally held in one of said needle eyes with the head being stopped outside said needle eye against a surface of said arm.

5. The device of claim 1, wherein the body further comprises a securing clamp for receiving by snap-fitting and holding the guide rod against the body, said securing clamp being further from said arms than said guide stop.

6. A dental floss for use with a dental device comprising:
an intermediate floss part having two opposite ends;
a guide rod integrally connected to one end of the intermediate floss part; and
a stop button integrally connected to another end of the intermediate floss part.

7. The dental floss of claim 6, wherein the stop button is mushroom-shaped with a head and a foot.

8. The dental floss of claim 6, wherein the guide rod has a gripping protuberance at one end.

9. The dental floss of claim 6, wherein the guide rod and the stop button are made from rigid plastic material by integrally molding the ends of the intermediate floss part.

10. The dental floss of claim 6, wherein a plurality of pieces of the dental floss are arranged side by side in a plane, the stop button of each piece of dental floss connected by a first connection to a first frame piece of a unitary frame and the guide rod of each length of dental floss connected by a second connector to a opposing second frame piece of the unitary frame.

11. The dental floss of claim 10, wherein said plurality of pieces of dental floss and said unitary frame are integrally molded.

12. The dental floss of claim 11, wherein said first and second connectors have a small cross section so that a piece of dental floss may be easily removed from said frame.

13. A dental floss for use with a dental device having two separated arms, each arm having a needle eye of predetermined cross-section near a free end, the needle eye generally opposing one another with the two arms being separated by a predetermined distance, the dental floss comprising:
an intermediate floss part having two opposite ends and a length greater than said predetermined distance;
a guide rod integrally connected to one end of the intermediate floss part, said rod having a cross-section smaller than said needle eye; and
a stop button integrally connected to another end of the intermediate floss part, said button having a cross-section greater than said needle eyes.

14. The dental floss of claim 13, wherein the stop button is mushroom-shaped with a head and a foot, the foot having a cross-section adapted to be frictionally held in one of said needle eyes with the head being stopped against a surface of the arm around said needle eye.

15. The dental floss of claim 13, wherein the guide rod has a length greater than said distance.

16. The dental floss of claim 13, wherein the guide rod has a gripping protuberance at one end.

17. The dental floss of claim 13, wherein the guide rod and the stop button are made from rigid plastic material by integrally molding the ends of the length of the intermediate floss part.

* * * * *